United States Patent

Johnson et al.

[11] Patent Number: 4,568,348
[45] Date of Patent: Feb. 4, 1986

[54] KNEE PROSTHESIS

[75] Inventors: Robert Johnson, Hoylake; Martin A. Elloy, Liverpool, both of England

[73] Assignee: Chas. F. Thackray Limited, Leeds, United Kingdom

[21] Appl. No.: 474,801

[22] Filed: Mar. 14, 1983

[30] Foreign Application Priority Data

Mar. 13, 1982 [GB] United Kingdom ............... 8207376

[51] Int. Cl.$^4$ .............................................. A61F 1/04
[52] U.S. Cl. .................................... 623/20; 128/92 C
[58] Field of Search ............. 128/92 C; 3/1.91, 1.911, 3/1

[56] References Cited

U.S. PATENT DOCUMENTS 4,167,047  9/1979  Grundei et al. ................... 3/1.911
4,207,627  6/1980  Cloutier ............................ 3/1.911
4,224,696  9/1980  Murray et al. .................... 3/1.911

Primary Examiner—R. J. Apley
Assistant Examiner—David J. Isabella
Attorney, Agent, or Firm—Brooks & Kushman

[57] ABSTRACT

This invention relates to endo-prosthetic knee joint devices.

A knee prosthesis according to the invention comprises a femoral component for attachment to the femur and having a bearing surface including a first inferior curved portion and a second posterior portion contiguous with and of relatively lesser curvature than said first portion, a tibial component for attachment to the tibia and having a concave bearing surface and a meniscal component to lie between the femoral and tibial components and having bearing surfaces complementary to said first portion of the bearing surface of the femoral component and to the bearing surface of the tibial component.

8 Claims, 4 Drawing Figures

KNEE PROSTHESIS

This invention relates to endo-prosthetic knee joint devices.

Knee prostheses may be of the "constrained" type or of the "non-constrained" type. The former type replaces the functions of the bearing surfaces and of the ligaments and may take the form of a hinge. The latter types makes use of some or all of the natural ligaments to control the mode of articulation and/or prevent the separation of the opposing bearing surfaces of the prosthesis. This invention is concerned with knee prostheses of the non-constrained type.

Known knee prostheses comprise a tibial component in the form of plastic inserts located in metal supports. Plastic inserts are provided with bearing surfaces and a femoral component is provided with complementary bearing surfaces. Such devices only allow relative axial rotation where there is noncongruity of the opposing bearing surfaces. Furthermore, the metal support of the tibial component serves only as a reinforcement of the plastic inserts and as an aid to cemented fixation.

Other knee prostheses have been proposed which include meniscal components. However, such components are able only to move forwards or backwards to compensate for a fixed axis of flexion in the femoral component.

A natural knee articulates both in flexion and rotation, the freedom to rotate increasing from zero at full extension to a maximum at full flexion. Flexion occurs about an axis which lies approximately perpendicular to the tibia and parallel to the frontal plane. This axis is, however, not fixed but moves backwards as flexion increases. Rotation occurs about the long axis of the tibia. The locus of the flexion axis and the limit to rotational freedom is determined by the shapes of the opposing bearing surfaces (condyles) of femur and tibia and also the inextensative length and positions of insertion of four ligaments which connect the femur to the tibia. These ligaments comprise two collateral ligaments and two cruciate ligaments. Non-congruity of opposing condyles allows a complex articulation. Load distribution is achieved by two intervening semi-lunar cartilages or meniscii. These meniscii approximately conform to the femoral surfaces and are free to move relative to the tibial condyles.

According to the present invention there is provided a knee prosthesis comprising a femoral component for attachment to the femur and having a bearing surface which is cylindrical about medio-lateral axes and includes a first inferior curved portion and a second posterior curved portion contiguous in a tangential relationship with and of relatively lesser curvature than said first curved portion, a tibial component for attachment to the tibia and having a concave bearing surface and a meniscal component to lie between the femoral and tibial components and having bearing surfaces complementary to said first curved portion of the bearing surface of the femoral component and to the bearing surface of the tibial component, and the complementary bearing surfaces of the meniscal and tibial components being conical such that relative axial rotation is possible between the tibial and meniscal components.

Preferably the femoral component replaces the bearing surfaces of both condyles and the patellar bearing area. More preferably the femoral component is made of metal.

Preferably the tibial component replaces the tibial plateaux and is made of metal.

Preferably the meniscal component is made of plastics.

The upper bearing surface of the tibial component preferably has an axis of generation parallel to the long axis of the tibia. The under surface of the meniscal component is complementary to that of the tibial component so that it rests congruously within it in a stable condition under gravity and the shapes of these complementary bearing surfaces are such that relative axial rotation is possible between the tibial and meniscal components. Preferably the bearing surfaces are shaped so that, under the influence of forces perpendicular to the tibial axis, the meniscal component is capable of riding up the side of the tibial bearing surface (subluxating).

The upper meniscal bearing surface is shaped as a surface of generation about a medio-lateral axis. At full extension the first inferior curved portion of the femoral component and the upper bearing surface of the meniscal component are congruous allowing relative movement only about the medio-lateral axis of flexion. These bearing surfaces are cylindrical and more preferably shoulders are provided at the ends of the meniscal upper bearing tracks which engage the axial ends (cheeks) of the femoral bearing tracks. As a result medio-lateral relative movement parallel to the axis of flexion is resisted.

The second posterior (back) bearing surface of the femoral component is of reduced lateral curvature which is continuous with and tangential to the inferior (under) surface and which preferably has an axis of generation lying behind that of the inferior surface. On flexion of the knee, the posterior femoral surface comes into contact with the upper meniscal surface so that the axis of flexion moves backwards in a similar manner to that of the natural knee. In such a flexed position the femoral and meniscal bearing surfaces are no longer congruous but do have parallel axes of generation (in line contact) and as a result are capable only of limited forward or backward movement in addition to unrestricted flexion. By a suitable choice of the lateral radii of the femoral component stable flexion of the prosthesis is capable under the control of the collateral ligaments, with sliding movement occurring between the femoral component and the meniscal component. Prosthetic rotation about the tibial axis is free to occur between the meniscal and tibial components, the degree of rotation being controlled only by the collateral ligaments. In this way it is impossible to transmit axial torque through the prosthesis and, therefore, prosthetic fixation is not jeopardised.

If desired a patellar button may be provided.

The meniscal component may be provided in various thicknesses in order to compensate for surgical inaccuracy.

An embodiment of the present invention will now be described, by way of example only, and with reference to the accompanying drawings, in which.

Figure 1A:
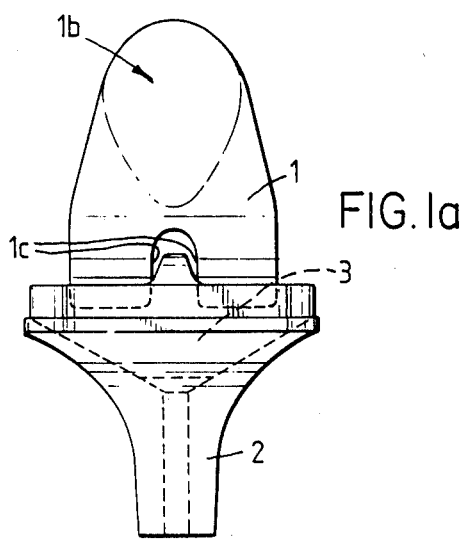
FIGS. 1a and 1b are respectively front and side elevations of a knee prosthesis in accordance with the present invention.
Figure 1B:
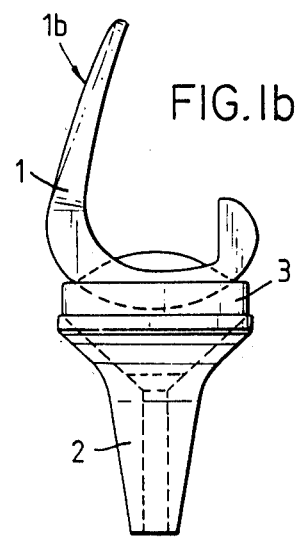

Referring to the drawings, a knee prosthesis in accordance with the present invention includes a metal femoral component 1 which is a surface replacement element having two condylar tracks 1a joined by a patellar bearing surface 1b. The condylar bearing surfaces are tangential cylindrical surfaces about medio-lateral axes. The inferior and posterior radii of these surfaces, R and r respectively, approximate to the corresponding radii of curvature of the natural femur.

Between the two condylar tracks 1a is a gap approximating to the inter-condylar notch of the natural femur. The inner edges of the tracks are upturned to produce medio-lateral bearing areas 1c on either side of the inter-condylar notch.

The bone faces of the prosthesis are provided by re-entrant forms to provide for cement keying.

The metal tibial component 2 comprises a conical dish having a stem 2d extending from the apex thereof. Upper bearing surface 2a is in the shape of a concave cone (of included angle $\theta$) about the vertical (tibial) axis. The front 2c and back edges of the dish are cropped back to fit within the confines of the tibial plateaux. Stem 2d, extending from the underside of the dish, is suitably shaped to fit into the medullar of the tibia. Central hole 2e, coaxial to the long axis of the tibia, is provided for alignment purposes.

The meniscal component 3 has a horizontal plan profile and an inferior conical bearing surface 3a complementary to that of the tibial component.

The superior surface of meniscal component 3 has two co-axial cylindrical tracks 3b of radius R complementary to the inferior condylar bearing surfaces of the femoral component. Between the bearing tracks a raised portion 3c provides bearing counterfaces for femoral bearing surfaces 1c and thereby resisting relative medio-lateral movements.

Figure 2:
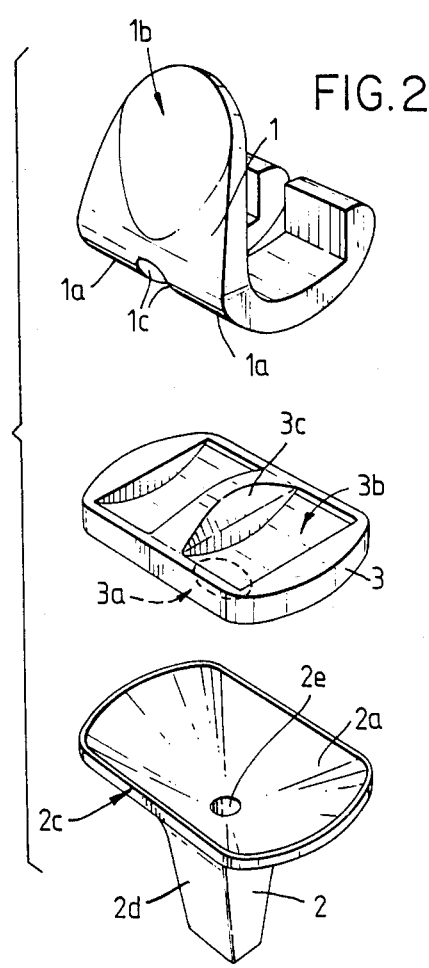
FIG. 2 is an exploded perspective view of the knee prosthesis of FIG. 1.
Figure 3:
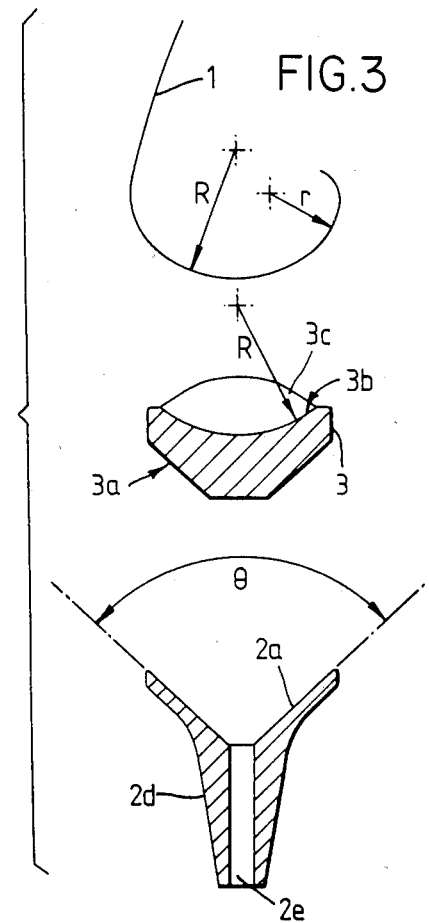
FIG. 3 is a further exploded view of the knee prosthesis of FIG. 1, showing the elements diagrammatically to illustrate the shapes of the various bearing surfaces.

Both the tibial conical surface 2a and the meniscal conical surface 3a have straight line elements thereon extending from the vertices thereof as illustrated in FIG. 3. Such a construction permits relative axial rotation between the tibial and meniscal components while still providing a construction that is relatively easy to manufacture just like the cylindrically curved femoral and meniscal bearing surfaces 1a and 3b illustrated in FIG. 2.

The meniscal component may be made in various thicknesses to allow for compensation of surgical error.

The above-described knee prosthesis may be inserted in a patient by means of a range of instruments which are simple to use and which facilitate anatomical positioning of the femoral component, i.e. condylar axis at 7° nominal to femoral diaphyseal axis. The instruments allow tibial location into sound bone and true to the long axis of the tibia and also selection of meniscal components to take up ligamentous slackness to produce stable articulation.

The above-described knee prosthesis provides femoro-menisco articulation which is polycentric flexion and menisco-tibial articulation which is uniaxilar rotation. Medio-lateral femoro-meniscal movement is blocked and menisco-tibial subluxation perpendicular to tibial axis allows ligaments to resist abnormal forces. There is no capability for transmitting torsional load through prosthesis/bone interfaces. The prosthesis provides natural articulation under control of collateral ligaments. The menisco-tibial rotation allows natural axial orientation to occur regardless of the cemented position. By containment of the meniscal component with the dished tibial component, plastic extrusion is resisted so that special reinforcement of the meniscal component is not required.

We claim:

1. A knee prosthesis comprising a femoral component for attachment to the femur and having a bearing surface which is cylindrically curved about medio-lateral axes without any curvature along the medio-lateral axes, said femoral component bearing surface including a first inferior cylindrically curved portion about a medio-lateral axis and also including a second posterior cylindrically curved portion about a medio-lateral axis, said second posterior curved portion being contiguous in a tangential relationship with and of relatively lesser curvature than said first curved portion, a tibial component for attachment to the tibia and having a concave bearing surface, and a meniscal component between the femoral and tibial components and having bearing surfaces complementary to said first curved portion of the bearing surface of the femoral component and to the bearing surface of the tibial component, the complementary bearing surfaces of the meniscal and tibial components being conical with straight line elements thereon extending from the vertices thereof such that relative axial rotation is possible between the tibial and meniscal components.

2. A knee prosthesis in accordance with claim 1, in which the femoral component replaces the bearing surface of both condyles and the patella bearing area.

3. A knee prosthesis in accordance with claim 1, in which the femoral component is made of metal.

4. A knee prosthesis in accordance with claim 1, in which the tibial component replaces the tibial plateaux and is made of metal.

5. A knee prosthesis in accordance with claim 1, in which said meniscal and tibial bearing surfaces are shaped so that, under the influence of forces perpendicular to the tibial axis, the meniscal component is capable of riding up the side of the tibial bearing surface.

6. A knee prosthesis in accordance with claim 1, in which the meniscal component has spaced bearing tracks that include end shoulders, and the femoral component having spaced bearing tracks including ends that engage the end shoulders of the bearing tracks of the meniscal component to prevent medio-lateral movement between the femoral and meniscal components.

7. A knee prosthesis in accordance with claim 1, in which the second posterior curved bearing surface portion of the femoral component is tangential to the first inferior curved bearing surface portion of the femoral component extending about an axis lying behind the first curved bearing surface portion.

8. A knee prosthesis in accordance with claim 1, in which the meniscal component is made of plastic.

* * * * *